(12) United States Patent
Burbank et al.

(10) Patent No.: US 9,510,809 B2
(45) Date of Patent: *Dec. 6, 2016

(54) TISSUE SPECIMEN ISOLATING AND DAMAGING DEVICE AND METHOD

(71) Applicant: SenoRx, Inc., Tempe, AZ (US)

(72) Inventors: Fred H. Burbank, Laguna Niguel, CA (US); Paul Lubock, Monarch Beach, CA (US)

(73) Assignee: SenoRx, Inc., Tempe, AZ (US)

( * ) Notice: Subject to any disclaimer, the term of this patent is extended or adjusted under 35 U.S.C. 154(b) by 335 days.

This patent is subject to a terminal disclaimer.

(21) Appl. No.: 14/165,116

(22) Filed: Jan. 27, 2014

(65) Prior Publication Data

US 2014/0180163 A1   Jun. 26, 2014

Related U.S. Application Data

(60) Continuation of application No. 12/082,509, filed on Apr. 11, 2008, now Pat. No. 8,636,734, which is a
(Continued)

(51) Int. Cl.
*A61B 18/14* (2006.01)
*A61B 10/02* (2006.01)
(Continued)

(52) U.S. Cl.
CPC ....... *A61B 10/0233* (2013.01); *A61B 10/0266* (2013.01); *A61B 17/00234* (2013.01);
(Continued)

(58) Field of Classification Search
CPC .............. A61B 18/1487; A61B 2018/00214; A61B 2018/00333; A61B 2018/144;A61B 2018/00577; A61B 2018/1861; A61B 2018/00601; A61B 2018/00202; A61B 10/02; A61B 10/0266
See application file for complete search history.

(56) References Cited

U.S. PATENT DOCUMENTS

| 2,032,860 A | 3/1936 | Wappler et al. |
| 2,447,169 A | 8/1948 | De Sousa |

(Continued)

FOREIGN PATENT DOCUMENTS

| DE | 1225813 B | 9/1966 |
| DE | 3804849 A1 | 9/1988 |

(Continued)

OTHER PUBLICATIONS

Armstrong, J.S. et al., "Differential marking of excision planes in screened breast lesions by organically coloured gelantins", Journal of Clinical Pathology, (Jul. 1990), 43(7) 604-7, XP000971447 abstract; tables 1 and 2.
(Continued)

*Primary Examiner* — Michael Peffley

(57) ABSTRACT

A device and method for treatment of a tissue specimen disposed in surrounding tissue includes isolating the tissue specimen from the surrounding tissue by using a separating device to sever and separate the tissue specimen from the surrounding tissue; damaging the isolated tissue specimen with a tissue specimen damaging device; and using an encapsulating device to encapsulate the isolated and damaged tissue specimen, the encapsulating device configured for operation independent from the separating device and the tissue specimen damaging device.

18 Claims, 8 Drawing Sheets

Related U.S. Application Data division of application No. 10/756,178, filed on Jan. 13, 2004, now Pat. No. 7,357,801, which is a continuation of application No. 09/884,349, filed on Jun. 18, 2001, now Pat. No. 6,676,658, which is a continuation of application No. 09/238,965, filed on Jan. 27, 1999, now Pat. No. 6,659,105.

(51) Int. Cl.

| | | |
|---|---|---|
| *A61B 17/00* | (2006.01) | |
| *A61B 17/3205* | (2006.01) | |
| *A61B 17/3207* | (2006.01) | |
| *A61B 18/02* | (2006.01) | |
| *A61B 18/06* | (2006.01) | |
| *A61B 18/20* | (2006.01) | |
| A61B 17/221 | (2006.01) | |
| A61B 17/34 | (2006.01) | |
| A61B 18/00 | (2006.01) | |
| A61B 18/12 | (2006.01) | |
| A61B 18/16 | (2006.01) | |
| A61B 18/18 | (2006.01) | |
| A61N 5/10 | (2006.01) | |

(52) U.S. Cl.
CPC .. *A61B 17/00491* (2013.01); *A61B 17/32056* (2013.01); *A61B 17/320725* (2013.01); *A61B 18/0206* (2013.01); *A61B 18/06* (2013.01); *A61B 18/14* (2013.01); *A61B 18/1482* (2013.01); *A61B 18/20* (2013.01); *A61N 5/1007* (2013.01); A61B 10/02 (2013.01); A61B 17/221 (2013.01); A61B 17/3417 (2013.01); A61B 18/148 (2013.01); A61B 18/1487 (2013.01); A61B 18/1492 (2013.01); A61B 90/37 (2016.02); A61B 2010/0208 (2013.01); A61B 2017/00287 (2013.01); A61B 2017/2212 (2013.01); A61B 2017/320733 (2013.01); A61B 2017/3488 (2013.01); A61B 2018/0091 (2013.01); A61B 2018/00208 (2013.01); A61B 2018/00214 (2013.01); A61B 2018/00267 (2013.01); A61B 2018/00333 (2013.01); A61B 2018/00577 (2013.01); A61B 2018/00601 (2013.01); A61B 2018/00898 (2013.01); A61B 2018/00916 (2013.01); A61B 2018/126 (2013.01); A61B 2018/1253 (2013.01); A61B 2018/144 (2013.01); A61B 2018/1407 (2013.01); A61B 2018/1425 (2013.01); A61B 2018/1475 (2013.01); A61B 2018/162 (2013.01); A61B 2018/1861 (2013.01); A61B 2090/3908 (2016.02); A61N 5/1027 (2013.01)

(56) References Cited

U.S. PATENT DOCUMENTS

| | | | |
|---|---|---|---|
| 3,598,108 | A | 8/1971 | Jamshidi et al. |
| 3,805,791 | A | 4/1974 | Seuberth et al. |
| 3,844,272 | A | 10/1974 | Banko |
| 3,847,153 | A | 11/1974 | Weissman |
| 3,910,279 | A | 10/1975 | Okada et al. |
| 3,945,375 | A | 3/1976 | Banko |
| 3,955,578 | A | 5/1976 | Chamness et al. |
| 4,007,732 | A | 2/1977 | Kvavle et al. |
| 4,202,338 | A | 5/1980 | Bitrolf |
| 4,243,048 | A | 1/1981 | Griffin |
| 4,294,254 | A | 10/1981 | Chamness |
| 4,311,143 | A | 1/1982 | Komiya |
| 4,362,160 | A | 12/1982 | Hiltebrandt |
| 4,425,908 | A | 1/1984 | Simon |
| 4,493,320 | A | 1/1985 | Treat |
| 4,503,855 | A | 3/1985 | Maslanka |
| 4,532,924 | A | 8/1985 | Auth et al. |
| 4,565,200 | A | 1/1986 | Cosman |
| 4,576,162 | A | 3/1986 | McCorkle |
| 4,592,356 | A | 6/1986 | Gutierrez |
| 4,611,494 | A | 9/1986 | Uchiyama |
| 4,611,594 | A | 9/1986 | Grayhack et al. |
| 4,616,656 | A | 10/1986 | Nicholson |
| 4,638,802 | A | 1/1987 | Okada |
| 4,643,187 | A | 2/1987 | Okada |
| 4,682,606 | A | 7/1987 | DeCaprio |
| 4,718,419 | A | 1/1988 | Okada |
| 4,724,836 | A | 2/1988 | Okada |
| 4,773,413 | A | 9/1988 | Hussein et al. |
| 4,774,948 | A | 10/1988 | Markham |
| 4,966,583 | A | 10/1990 | Debbas |
| 4,997,435 | A | 3/1991 | Demeter |
| 5,007,908 | A | 4/1991 | Rydell |
| 5,024,617 | A | 6/1991 | Karpiel |
| 5,035,696 | A | 7/1991 | Rydell |
| 5,037,379 | A | 8/1991 | Clayman et al. |
| 5,041,124 | A | 8/1991 | Kensey |
| 5,047,027 | A | 9/1991 | Rydell |
| 5,059,197 | A | 10/1991 | Urie |
| 5,064,424 | A | 11/1991 | Bitrolf |
| 5,066,295 | A | 11/1991 | Kozak et al. |
| 5,078,716 | A | 1/1992 | Doll |
| 5,080,660 | A | 1/1992 | Buelna |
| 5,085,659 | A | 2/1992 | Rydell |
| 5,100,423 | A | 3/1992 | Fearnot |
| RE33,925 | E | 5/1992 | Bales et al. |
| 5,111,828 | A | 5/1992 | Kornberg et al. |
| 5,133,359 | A | 7/1992 | Kedem |
| 5,133,360 | A | 7/1992 | Spears |
| 5,133,713 | A | 7/1992 | Huang et al. |
| RE34,056 | E | 9/1992 | Lindgren et al. |
| 5,147,307 | A | 9/1992 | Gluck |
| 5,158,084 | A | 10/1992 | Ghiatas |
| 5,158,561 | A | 10/1992 | Rydell et al. |
| 5,163,938 | A | 11/1992 | Kambara et al. |
| 5,192,270 | A | 3/1993 | Carswell, Jr. |
| 5,196,007 | A | 3/1993 | Ellman et al. |
| 5,201,732 | A | 4/1993 | Parins et al. |
| 5,201,741 | A | 4/1993 | Dulebohn |
| 5,207,686 | A | 5/1993 | Dolgin |
| 5,215,521 | A | 6/1993 | Cochran et al. |
| 5,217,458 | A | 6/1993 | Parins |
| 5,221,269 | A | 6/1993 | Miller et al. |
| 5,221,281 | A | 6/1993 | Klicek |
| 5,224,488 | A | 7/1993 | Neuffer |
| 5,234,426 | A | 8/1993 | Rank et al. |
| 5,281,218 | A | 1/1994 | Imran |
| 5,295,990 | A | 3/1994 | Levin |
| 5,304,176 | A | 4/1994 | Phillips |
| 5,311,858 | A | 5/1994 | Adair |
| 5,312,400 | A | 5/1994 | Bales et al. |
| 5,318,564 | A | 6/1994 | Eggers |
| 5,323,768 | A | 6/1994 | Saito et al. |
| 5,324,288 | A | 6/1994 | Billings et al. |
| 5,330,483 | A | 7/1994 | Heaven et al. |
| 5,331,166 | A | 7/1994 | Yamamoto et al. |
| 5,335,671 | A | 8/1994 | Clement |
| 5,337,754 | A | 8/1994 | Heaven et al. |
| 5,344,420 | A | 9/1994 | Hilal et al. |
| 5,353,804 | A | 10/1994 | Kornberg et al. |
| 5,374,188 | A | 12/1994 | Frank et al. |
| 5,376,094 | A | 12/1994 | Kline |
| 5,380,321 | A | 1/1995 | Yoon |
| 5,395,312 | A | 3/1995 | Desai |
| 5,395,313 | A | 3/1995 | Naves et al. |
| 5,395,383 | A | 3/1995 | Adams et al. |
| 5,397,320 | A | 3/1995 | Essig et al. |
| 5,401,272 | A | 3/1995 | Perkins |
| 5,403,310 | A | 4/1995 | Fischer |
| 5,409,004 | A | 4/1995 | Sloan |
| 5,415,656 | A | 5/1995 | Tihon et al. |
| 5,417,687 | A | 5/1995 | Nardella et al. |

(56) References Cited

U.S. PATENT DOCUMENTS

| | | | |
|---|---|---|---|
| 5,417,697 A * | 5/1995 | Wilk | A61B 18/10 606/113 |
| 5,423,770 A | 6/1995 | Yoon | |
| 5,423,809 A | 6/1995 | Klicek | |
| 5,423,814 A | 6/1995 | Zhu et al. | |
| 5,431,649 A | 7/1995 | Mulier et al. | |
| 5,437,665 A | 8/1995 | Munro | |
| 5,441,498 A | 8/1995 | Perkins | |
| 5,441,503 A | 8/1995 | Considine et al. | |
| 5,445,142 A | 8/1995 | Hassler, Jr. | |
| 5,449,382 A | 9/1995 | Dayton | |
| 5,462,553 A | 10/1995 | Dolgin | |
| 5,470,308 A | 11/1995 | Edwards et al. | |
| 5,471,982 A | 12/1995 | Edwards et al. | |
| 5,477,862 A | 12/1995 | Haaga | |
| 5,484,436 A | 1/1996 | Eggers et al. | |
| 5,487,385 A | 1/1996 | Avitall | |
| 5,488,958 A | 2/1996 | Topel et al. | |
| 5,500,012 A | 3/1996 | Brucker et al. | |
| 5,501,654 A | 3/1996 | Failla et al. | |
| 5,501,694 A | 3/1996 | Ressemann et al. | |
| 5,507,743 A | 4/1996 | Edwards et al. | |
| 5,509,916 A | 4/1996 | Taylor | |
| 5,526,822 A | 6/1996 | Burbank et al. | |
| 5,527,298 A | 6/1996 | Vance et al. | |
| 5,527,331 A | 6/1996 | Kresch et al. | |
| 5,536,251 A | 7/1996 | Evard et al. | |
| 5,542,916 A | 8/1996 | Hirsch et al. | |
| 5,542,948 A | 8/1996 | Weaver et al. | |
| 5,549,108 A | 8/1996 | Edwards et al. | |
| 5,554,159 A | 9/1996 | Fischer | |
| 5,562,102 A | 10/1996 | Taylor | |
| 5,562,720 A | 10/1996 | Stern et al. | |
| 5,578,030 A | 11/1996 | Levin | |
| 5,578,031 A | 11/1996 | Wilk et al. | |
| 5,595,185 A | 1/1997 | Erlich | |
| 5,599,347 A | 2/1997 | Hart et al. | |
| 5,607,389 A | 3/1997 | Edwards et al. | |
| 5,611,803 A | 3/1997 | Heaven et al. | |
| 5,643,282 A | 7/1997 | Kieturakis | |
| 5,649,547 A | 7/1997 | Ritchart et al. | |
| 5,653,718 A | 8/1997 | Yoon | |
| 5,665,085 A | 9/1997 | Nardella | |
| 5,674,184 A | 10/1997 | Hassler, Jr. | |
| 5,676,663 A | 10/1997 | Kim | |
| 5,683,384 A | 11/1997 | Gough et al. | |
| 5,684,739 A | 11/1997 | Takeuchi | |
| 5,687,739 A | 11/1997 | McPherson et al. | |
| 5,697,946 A | 12/1997 | Hopper et al. | |
| 5,700,273 A | 12/1997 | Buelna et al. | |
| 5,715,825 A | 2/1998 | Crowley | |
| 5,730,726 A | 3/1998 | Klingenstein | |
| 5,733,283 A | 3/1998 | Malis et al. | |
| 5,735,289 A * | 4/1998 | Pfeffer | A61B 17/00234 600/562 |
| 5,735,847 A | 4/1998 | Gough et al. | |
| 5,741,225 A | 4/1998 | Lax et al. | |
| 5,743,906 A | 4/1998 | Parins et al. | |
| 5,749,887 A | 5/1998 | Heske et al. | |
| 5,752,972 A | 5/1998 | Hoogeboom | |
| 5,755,697 A | 5/1998 | Jones et al. | |
| 5,759,202 A | 6/1998 | Schroeppel | |
| 5,766,163 A | 6/1998 | Mueller et al. | |
| 5,769,086 A | 6/1998 | Ritchart et al. | |
| 5,769,794 A | 6/1998 | Conlan et al. | |
| 5,772,660 A | 6/1998 | Young et al. | |
| 5,782,775 A | 7/1998 | Milliman et al. | |
| 5,788,709 A | 8/1998 | Riek et al. | |
| 5,794,626 A | 8/1998 | Kieturakis | |
| 5,795,308 A | 8/1998 | Russin | |
| 5,797,907 A | 8/1998 | Clement | |
| 5,800,445 A | 9/1998 | Ratcliff et al. | |
| 5,810,764 A | 9/1998 | Eggers et al. | |
| 5,810,806 A * | 9/1998 | Ritchart | A61B 10/0266 604/21 |
| 5,814,044 A | 9/1998 | Hooven | |
| 5,817,034 A | 10/1998 | Milliman et al. | |
| 5,823,971 A | 10/1998 | Robinson et al. | |
| 5,827,268 A | 10/1998 | Laufer | |
| 5,827,276 A | 10/1998 | LeVeen et al. | |
| 5,840,044 A | 11/1998 | Dassa et al. | |
| 5,848,978 A | 12/1998 | Cecchi | |
| 5,857,981 A | 1/1999 | Bucalo et al. | |
| 5,857,982 A | 1/1999 | Milliman et al. | |
| 5,868,740 A | 2/1999 | LeVeen et al. | |
| 5,879,357 A | 3/1999 | Heaton et al. | |
| 5,882,316 A | 3/1999 | Chu et al. | |
| 5,902,272 A | 5/1999 | Eggers et al. | |
| 5,913,857 A | 6/1999 | Ritchart et al. | |
| 5,925,044 A | 7/1999 | Hoffmann et al. | |
| 5,928,164 A | 7/1999 | Burbank et al. | |
| 5,941,869 A | 8/1999 | Patterson et al. | |
| 5,947,964 A | 9/1999 | Eggers et al. | |
| 5,951,550 A | 9/1999 | Shirley et al. | |
| 5,954,670 A | 9/1999 | Baker | |
| 5,980,469 A | 11/1999 | Burbank et al. | |
| 5,984,919 A | 11/1999 | Hilal et al. | |
| 5,984,920 A | 11/1999 | Steinbach | |
| 6,004,269 A | 12/1999 | Crowley et al. | |
| 6,022,362 A | 2/2000 | Lee et al. | |
| 6,032,673 A | 3/2000 | Savage et al. | |
| 6,036,681 A | 3/2000 | Hooven | |
| 6,050,955 A | 4/2000 | Bryan et al. | |
| 6,050,992 A | 4/2000 | Nichols | |
| 6,059,734 A | 5/2000 | Yoon | |
| 6,063,082 A | 5/2000 | DeVore et al. | |
| 6,090,105 A | 7/2000 | Zepeda et al. | |
| 6,106,542 A | 8/2000 | Toybin et al. | |
| 6,117,153 A | 9/2000 | Lary et al. | |
| 6,120,462 A | 9/2000 | Hibner et al. | |
| 6,126,656 A | 10/2000 | Billings | |
| 6,135,997 A | 10/2000 | Laufer et al. | |
| 6,142,955 A | 11/2000 | Farascioni et al. | |
| 6,261,241 B1 | 7/2001 | Burbank et al. | |
| 6,277,083 B1 | 8/2001 | Eggers et al. | |
| 6,280,450 B1 | 8/2001 | McGuckin, Jr. | |
| 6,312,429 B1 | 11/2001 | Burbank et al. | |
| 6,331,166 B1 * | 12/2001 | Burbank | A61B 17/00491 600/567 |
| 6,344,026 B1 | 2/2002 | Burbank et al. | |
| 6,363,940 B1 | 4/2002 | Krag | |
| 6,383,145 B1 | 5/2002 | Worm et al. | |
| 6,454,727 B1 | 9/2002 | Burbank et al. | |
| 6,471,700 B1 | 10/2002 | Burbank et al. | |
| 6,488,636 B2 | 12/2002 | Bryan et al. | |
| 6,494,881 B1 | 12/2002 | Bales et al. | |
| 6,497,706 B1 | 12/2002 | Burbank et al. | |
| 6,508,773 B2 | 1/2003 | Burbank et al. | |
| 6,514,248 B1 | 2/2003 | Eggers et al. | |
| 6,540,693 B2 | 4/2003 | Burbank et al. | |
| 6,540,695 B1 | 4/2003 | Burbank et al. | |
| 6,638,234 B2 | 10/2003 | Burbank et al. | |
| 6,679,851 B2 | 1/2004 | Burbank et al. | |
| 6,689,071 B2 | 2/2004 | Burbank et al. | |
| 6,689,145 B2 | 2/2004 | Lee et al. | |
| 6,699,206 B2 | 3/2004 | Burbank et al. | |
| 6,702,831 B2 | 3/2004 | Lee et al. | |
| 6,712,775 B2 | 3/2004 | Burbank et al. | |
| 6,716,179 B2 | 4/2004 | Burbank et al. | |
| 6,758,848 B2 | 7/2004 | Burbank et al. | |
| 6,764,495 B2 | 7/2004 | Lee et al. | |
| 6,849,080 B2 | 2/2005 | Lee et al. | |
| 6,863,676 B2 | 3/2005 | Lee et al. | |
| 6,958,044 B2 | 10/2005 | Burbank et al. | |
| 6,997,885 B2 | 2/2006 | Lubock et al. | |
| 7,192,430 B2 * | 3/2007 | Truckai | A61B 18/1482 606/180 |
| 7,229,418 B2 | 6/2007 | Burbank et al. | |
| 7,261,712 B2 | 8/2007 | Burbank et al. | |
| 7,264,596 B2 | 9/2007 | Burbank et al. | |
| 7,322,938 B2 | 1/2008 | Burbank et al. | |
| 7,322,939 B2 | 1/2008 | Burbank et al. | |
| 7,322,940 B2 | 1/2008 | Burbank et al. | |
| 7,329,228 B2 | 2/2008 | Burbank et al. | |

(56) References Cited

U.S. PATENT DOCUMENTS

| | | |
|---|---|---|
| 7,377,902 B2 | 5/2008 | Burbank et al. |
| 8,152,737 B2 | 4/2012 | Burbank et al. |
| 8,229,553 B2 | 7/2012 | Burbank et al. |
| 2001/0002250 A1 | 5/2001 | Burbank et al. |
| 2002/0068879 A1 | 6/2002 | Lubock et al. |
| 2002/0077628 A1 | 6/2002 | Burbank et al. |
| 2003/0004407 A1 | 1/2003 | Carroll et al. |
| 2003/0144605 A1 | 7/2003 | Burbank et al. |
| 2003/0144805 A1 | 7/2003 | Shinohira |
| 2004/0167431 A1 | 8/2004 | Burbank et al. |
| 2004/0167432 A1 | 8/2004 | Burbank et al. |
| 2004/0176789 A1 | 9/2004 | Lee et al. |
| 2005/0004492 A1 | 1/2005 | Burbank et al. |
| 2005/0010131 A1 | 1/2005 | Burbank et al. |
| 2005/0187490 A1 | 8/2005 | Burbank et al. |
| 2005/0187491 A1 | 8/2005 | Burbank et al. |
| 2005/0197593 A1 | 9/2005 | Burbank et al. |
| 2006/0094983 A1 | 5/2006 | Burbank et al. |
| 2008/0077045 A1 | 3/2008 | Burbank et al. |
| 2012/0277626 A1 | 11/2012 | Burbank et al. |

FOREIGN PATENT DOCUMENTS

| | | |
|---|---|---|
| DE | 19528440 A1 | 2/1997 |
| EP | 0146699 A1 | 7/1985 |
| EP | 0509670 A2 | 10/1992 |
| EP | 0601709 A2 | 6/1994 |
| EP | 0667126 A1 | 8/1995 |
| EP | 0769281 A2 | 10/1995 |
| EP | 0797957 A1 | 10/1997 |
| EP | 0858774 A2 | 8/1998 |
| EP | 0970658 A1 | 12/2000 |
| FR | 2746628 A1 | 10/1997 |
| GB | 2311468 A | 2/1997 |
| WO | 9307811 A1 | 4/1993 |
| WO | 9313718 A1 | 7/1993 |
| WO | 9404220 A1 | 3/1994 |
| WO | 9427670 A1 | 12/1994 |
| WO | 9502370 A2 | 1/1995 |
| WO | 9502371 A2 | 1/1995 |
| WO | 9503843 A1 | 2/1995 |
| WO | 9510317 A1 | 4/1995 |
| WO | 9713460 A1 | 4/1997 |
| WO | 9729702 A1 | 8/1997 |
| WO | 9735522 A1 | 10/1997 |
| WO | 9804441 A1 | 2/1998 |
| WO | 9806346 A1 | 2/1998 |
| WO | 9824372 A1 | 6/1998 |
| WO | 9843531 A1 | 10/1998 |
| WO | 9904704 A2 | 2/1999 |
| WO | 9944506 A1 | 9/1999 |
| WO | 0012009 A2 | 3/2000 |
| WO | 0016697 A2 | 3/2000 |
| WO | 0044295 A1 | 8/2000 |
| WO | 0074561 A1 | 12/2000 |
| WO | 0105320 A1 | 1/2001 |
| WO | 0222023 A1 | 3/2002 |
| WO | 2005063126 A2 | 7/2005 |

OTHER PUBLICATIONS

Lorenzen,T. et al., The Loop Electrode: a New Device for US-guided Interstitial Tissue Ablation Using Radio frequency Electrosurgery—An Animal Study, 1996 Blackwell Science Ltd. Min Incas Ther & Allied Technol, pp. 5.511-5.516.

Burbank, F., M.D., Stereotactic Breast Biopsy: Its History, Its Present, and Its Future, The American Surgeon, Feb. 1996, vol. 62, pp. 128-150.

Micklos, Timothy J., Percutaneous Biopsy Techniques, Manual of Oncologic Therapeutics (1989/1990) pp. 39-42.

Hausner, K, "Laser Vs Electrosurgery", www.netvs.com/elmed/lasyselec.htm, May 19, 1998, pp. 1-4.

"The Dangers of Monopolar Electrosurgery and the Advantages of Bipolar Electrosurgery", Everest Medical, Technical Reviews; www.pycco.com/emdtechrvws.html, May 26, 1998, pp. 1-9.

Nolsoe, Christian P., et al., "Interstitial Hyperthermia of Colorectal Liver Metastases with a US-guided Nd-YAG Laser with a Diffuser Tip: A Pilot Clinical Study", Radiology, May 1993, vol. 187, pp. 333-337.

Amin, Zehir, MRCP et al., "Hepatic Metastases: Interstitial Laser Photocoagulation with Real-Time US Monitoring and Dynamic CT Evaluation of Treatment", Radiology, May 1993; vol. 187, pp. 339-347.

Bown, S. G. , "Phototherapy of Tumors", World Journal of Surgery, 1983, vol. 7, pp. 700-709, University College Hospital, London, United Kingdom.

Storm, et al., "Clinical Thermochemotherapy, A Controlled Trial in Advanced Cancer Patients", Cancer, Feb. 15, 1984, pp. 863-868, vol. 53.

Jacques, et al., "Liver photocoagulation with diode laser (805 nm) vs Nd:YAG laser (1064 nm)", SPIE vol. 1646 Laser-Tissue Interaction III 1992, pp. 107-125.

Jolesz, et al., "MR Imaging of Laser-Tissue Interactions", Magnetic Resonance Imaging, Radiology, Jul. 1988; pp. 249-253, vol. 168.

Anzai, et al., "Nd:YAG Interstitial Laser Phototherapy Guided by Magnetic Resonance Imaging in an Ex Vivo Model: Dosimetry of Laser-MR-Tissue Interaction", Laryngoscope 101: Jul. 1991, pp. 755-760.

Le Bihan, et al., "Temperature Mapping with MR Imaging of Molecular Diffusion; Application to Hyperthermia", Therapeutic Radiology, Radiology, Jun. 1988, pp. 853-857, vol. 171.

Masters, et al., "Interstitial Laser Hyperthermia in Tumour Therapy", Annales Chirugiae et Gynaecologiae 79: 244-251, 1990.

Harries, et al., "Interstitial laser photocoagulation as a treatment for breast cancer", British Journal of Surgery 1994, 81, 1617-1619.

"Ultrasound-Guided Cryosurgery for Tumor Ablation", Mar. 22, 1995, Sheraton Boston Hotel & Towers, Boston, MA, Sponsored by: Deconess Hospital.

Gehman, et al., "High Dose Rate Endovascular Irradiation; Tolerance of Normal Tissues", Endocurietherapy/Hyperthermia Oncology, Jul. 1994, vol. 10, pp. 167-171, ISSN 8756-1687.

Bottcher, et al. "Endovascular Irradiation—A New Method to Avoid Recurrent Stenosis After Stent Implantation in Peripheral Arteries: Technique and Preliminary Results", 34th Annual ASTRO Meeting, San Diego, CA, Nov. 1992, International Journal of Radiation Oncology Biol. Phys., vol. 29, No. 1, pp. 183-186, 1994.

Fletcher, G. H., "Textbook of Radiotherapy" Third Edition, Lea & Febiger, 1980, Philadelphia.

Cox, J. D., "Moss' Radiation Oncology: Rationale, Technique, Results" Seventh Edition, Mosby 1994.

Doss, et al., "HDR Brachytherapy for Osteolytic Metastases in Previously Irradiated Sites", International Brachytherapy, Chapter 101, Sep. 1992, pp. 412-415, Memorial Regional Cancer Center, Modesto, CA.

Desinger, et al., "A New Application System for Simultaneous Laser and Ultrasonic Transmission in Endoscopic Surgery (LUST)", Surgical Applications of Energy, 94, vol. 3249 Apr. 2, 1998, San Jose, CA.

Desinger, et al., "Interstitial bipolar RF-thermotherapy (RFITT) Therapy planning by computer simulation and MRI-monitoring—A new concept for minimally invasive procedures -" Surgical Applications of Energy, 147, vol. 3249, Apr. 2, 1998, San Jose, CA.

Fucci, V., et al., "Large Bowel Transit Times Using Radioopaque Markers in Normal Cats", J. of Am. Animal Hospital Assn., Nov.-Dec. 1995 31 (6) 473-477.

Whitman, et al., Coaxial Core Needle Biopsy Under Mammographic Guidance: Indications and Applications, AJR:171, Jul. 1998, pp. 67-70.

Schindlbeck, N.E., et al., "Measurement of Colon Transit Time", J. of Gastroenterology, No. 28, pp. 399-404, 1990.

Pack, Mark S., M.D., Thomas, Robert S. M.D., "Axillary Lymph Node Dissection: Does It Have a Role in Primary Breast Cancer?", The American Surgeon, Feb. 1996, vol. 62, pp. 159-161.

Machine English Translation of German Application DE 195 28 440 A1, published Aug. 2, 1995.

(56) References Cited

OTHER PUBLICATIONS

International Search Report for PCT/US99/21416 mailed May 19, 2000.
Written Opinion of the International Searching Authority for PCT/US99/21416 dated Jul. 18, 2000.
International Search Report for PCT/US2005/027071 mailed Mar. 21, 2006.
International Search Report for PCT/US99/04471 mailed Jun. 14, 1999.

* cited by examiner

METHODS OF DAMAGING IN VIVO TISSUE SPECIMENS
100

| THERMAL TREATMENT | MECHANICAL TREATMENT | IONIZING RADIATION TREATMENT | CHEMICAL TREATMENT |
|---|---|---|---|
| 102 | 104 | 106 | 108 |
| LASER<br>HOT FLUIDS<br>COLD FLUIDS<br>RADIO FREQUENCY ENERGY<br>MICROWAVE<br>FOCUSSED ULTRASOUND<br>MECHANICAL ULTRASOUND<br>SCHOCK WAVES<br>RESISTIVE HEATING<br>CRYOSURGERY<br>CAUTERIZERS<br>HEATED OBJECTS | MORCELLATORS<br>OTHER CUTTING TECHNIQUES | X-RAYS (NEEDLE)<br>GAMMA RAYS<br>BRACHYTHERAPY SEEDS | ETHANOL<br>SOTRADECHOL<br>ACIDS<br>BASES<br>CHEMICAL COMPOUNDS<br>CHEMICAL MIXTURES<br>PHOTOREACTIVE CHEMICALS<br>SEALERS |

FIG. 4

TISSUE SPECIMEN ISOLATING AND DAMAGING DEVICE AND METHOD

RELATED APPLICATIONS

This is a continuation of application Ser. No. 12/082,509, filed Apr. 11, 2008, now U.S. Pat. No. 8,636,734, which is a divisional of application Ser. No. 10/756,178, filed Jan. 13, 2004, now U.S. Pat. No. 7,357,801, which is a continuation of application Ser. No. 09/884,349, filed Jun. 18, 2001, now U.S. Pat. No. 6,676,658, which is a continuation of application Ser. No. 09/238,965, filed Jan. 27, 1999, now U.S. Pat. No. 6,659,105. All of the above applications are incorporated by reference herein in their entirety and from which priority is claimed.

BACKGROUND OF THE INVENTION

1. Field of the Invention

This invention relates to treatment of tissue specimens and, more specifically, to the treatment of the tissue specimens in vivo.

2. Description of the Related Art

The prior art discloses devices and methods of isolating a tissue specimen while it remains in surrounding tissue. The prior art also discloses devices and methods of ablating or otherwise damaging a non-isolated tissue specimen in vivo. However, the prior art does not disclose, suggest, nor motivate combining the two concepts into one method or device. Additionally, the prior art does not disclose any synergistic effects of combining the two concepts.

It is disclosed in a paper entitled "The Loop Electrode: A New Device For US-guided Interstitial Tissue Ablation Using Radiofrequency Electrosurgery—An Animal Study," T. Lorentzen et al., Min Invas Ther & Allied Technol 1996: 5:511-516, that a radiofrequency loop is used to perform interstitial tissue ablation. The device was inserted into calf livers and rotated to interstitially cut off lesions. The paper reviews minimally invasive tissue ablation techniques, such as intraoperative cryosurgery and percutaneous methods such as laser, microwaves, radiofrequency electrosurgery, and injection of ethanol or hot saline. The paper also reviews high-focused ultrasound as an example of a non-invasive method. The paper does not disclose, suggest, nor motivate combining the use of a radiofrequency loop with other tissue ablation methods.

A procedure is disclosed in a paper entitled "Interstitial Hyperthermia Of Colorectal Liver Metastases With A US-guided Nd-YAG Laser with a Diffuser Tip: A Pilot Clinical Study," C. Nolsoe et al., Radiology, 1993; 187:333-337, that involves placing a laser fiber in the center of a tumor and irradiating the tumor to achieve hyperthermia ablation. It is also disclosed to use ultrasound to monitor the temperature of the tumor during the method. The paper discloses a charred border region about the tissue specimen and a coagulated region beyond the charred border. The paper does not disclose any concerns associated with ablating a nonisolated tissue specimen. The paper does not disclose, suggest, nor motivate combining the use of lasers with other tissue ablation methods.

It is disclosed in a paper entitled "Phototherapy of Tumors," S. G. Brown, World J. Surg. 7, 700-709, 1983, the use of the chemical hematoporphyrin derivative (HpD) in conjunction with a dye laser for tumor therapy. The HpD/dye laser method is not thermal, as is the case with most laser methods, but depends on the production of singlet oxygen by activated HpD. The paper discloses the promise of the HpD/dye laser methods—but with no disclosure, suggestion, or motivation to isolate the tissue specimen prior to treatment. The paper discloses the problems associated with unacceptable damage to surrounding tissue during thermal laser methods.

It is disclosed in a paper entitled "Clinical Thermochemotherapy: A Controlled Trial In Advanced Cancer Patients," F. K. Storm et al, Cancer 53:863868, 1984, to combine hyperthermia and chemotherapy for increased drug uptake of cancer cells. The hyperthermia was administered using a magnetrode magnetic loop induction device. The paper does disclose the beneficial of preserving the tissue surrounding the tissue specimen, which in the disclosed method is due to coincident vascular occlusion. It does not disclose, motivate, or suggest direct methods of severing vascular connections between a tissue specimen and surrounding tissue, in conjunction with other methods of tissue specimen ablation.

It is disclosed in a paper entitled "Liver Photocoagulation With Diode Laser (805 nm) Vs Nd:YAG Laser (1064 nm)," S. L. Jacques et al., SPIE Vol. 1646 Laser Tissue Interaction 111 (1992), p. 107-117, that laser treatment results in radially expanding regions of tissue damage. The paper does not disclose, suggest, nor motivate isolating the tissue specimen targeted for necrosis and any result that may have with reducing damage to surrounding tissue.

It is disclosed in a paper entitled "MR Imaging Of Laser-Tissue Interactions," F. A. Jolesz, Radiology 1989; 168:249-253, that thermal transfer and damage to surrounding tissue during hyperthermia treatment should be monitored. The paper also discloses that circulatory cooling, among other parameters, affects energy deposition. The paper does not disclose, suggest, nor motivate that isolating the tissue specimen prior to hyperthermia treatment. This information is similarly disclosed in a paper entitled "Temperature Mapping With MR Imaging Of Molecular Diffusion: Application to Hyperthermia," D. L. Bihan, Radiology 1989; 171: 853-857.

Therefore, the prior art discloses damage occurs to tissue surrounding a tissue specimen to be treated. What is needed is a device and method for reducing damage to the surrounding tissue. What is also needed is a device and method with increased efficiency for damaging the tissue specimens.

SUMMARY OF THE INVENTION

In an aspect of the invention, a tissue specimen that is disposed in surrounding tissue is treated. The treatment comprises an isolation step and a damaging step. During the isolation step, the tissue specimen is isolated from the surrounding tissue by at least partially severing the tissue specimen from the surrounding tissue. Next, the tissue specimen is damaged.

In an aspect of the invention, the isolating step further comprises the step of moving a tissue specimen isolating tool about the tissue specimen. In a further aspect of the invention, the tissue specimen isolating tool comprises a radio frequency energized wire. The treatment process may include the step of applying a tool charged with radio frequency energy to the tissue specimen.

In aspects of the invention, the damaging step may comprises applying ionizing radiation to the tissue specimen, cutting the tissue specimen, thermally treating the tissue specimen, chemically treating the tissue specimen, or seating an outer boundary of the tissue specimen.

In an aspect of the invention, a device for treatment of a tissue specimen in surrounding tissue comprises an operational portion, a tissue severing tool, and a tissue specimen damager. The tissue specimen isolating tool and the tissue specimen damager are disposed at the operational portion.

In a further aspect of the invention, a radio frequency generation source is functionally connected to the tissue specimen isolating, tool.

In an aspect of the invention, the tissue specimen isolating tool of the treatment device comprises a cutting member that is extendable to an outwardly radially bowed position about the operational portion. In a further aspect of the invention, a cutting member radio frequency generation source is functionally connected to the cutting member.

In an aspect of the invention, the tissue specimen damager of the treatment device comprises at least one metal member extending from the operational portion and being functionally connectable to a metal member radio frequency generation source.

In aspects of the invention, the tissue specimen damager may comprise an ionizing radiation director, a tissue specimen cutter, a thermal treatment system, or a chemical introduction system.

BRIEF DESCRIPTION OF THE DRAWINGS

FIG. 4 is a nonexclusive chart of treatment methods for damaging the tissue specimen according to embodiments of the invention.

DESCRIPTION OF THE PREFERRED EMBODIMENTS

Figure 1:
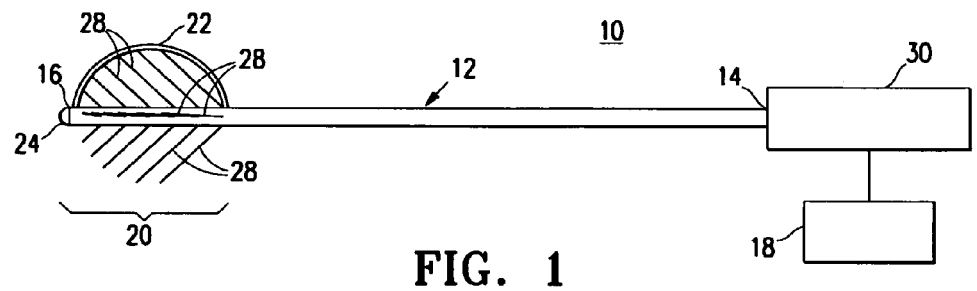
FIG. 1 shows a side view tissue specimen isolating and damaging device using radio frequency energized wires according to an embodiment of the invention.

Referring now to the figures, and specifically to FIG. 1, a tissue specimen isolating and damaging device 10 comprises a wand 12 having a proximal end 14 shown to the right and a distal end 16 shown to the left. The device 10 is used to isolate a tissue specimen while the tissue specimen is disposed in surrounding tissue and then damage the tissue specimen (see FIGS. 2 and 3). The isolation step may encompass isolating the tissue specimen from circulation and/or may encompass generally severing of the tissue specimen from the surrounding tissue. After the damaging step, the tissue specimen may remain in the body, turn into fibrotic tissue, and/or be removed from the body during the process or at a later time.

While isolating the tissue specimen may result in necrosis, the device 10 damages the tissue specimen to insure necrosis occurs. The necrosis of the tissue specimen results in reducing or eliminating the transfer of malignant or diseased tissue from the tissue specimen. The necrosis of the tissue specimen also dissuades the patient's body from repairing the tissue specimen. The shown embodiment of the invention utilizes a radio frequency generator 18 to perform the procedure. Other embodiments of the invention may use other methods, examples of which are non-exclusively discussed below.

Located at the distal end 16 of the wand 12 is an operational portion 20 of the device 10. The operational portion 20 is involved with both isolating and damaging the tissue specimen. In the shown embodiment, an outwardly radially bowed wire 22 isolates the tissue specimen. The wire 22 is disposed at the operational portion 20 and rotationally connected to the wand 12. In the shown embodiment of the invention, the wire 22 is initially in a retracted position against the wand 12 (not shown) to reduce trauma to surrounding tissue during placement of the device 10. The wire 22 is extended outward radially after the operational portion 20 is disposed in or proximate to the tissue specimen.

The wire 22, which is a tissue specimen isolating tool of the device 10, is powered by the radio frequency generator 18 and rotated to isolate the tissue specimen. As the wire 22 is rotated, a periphery channel (see FIG. 2) is formed between the tissue specimen and the surrounding tissue, thus severing the two. Other embodiments of the invention may have the wire 22 be fixedly and not rotatably connected to the wand 12, thus the whole wand is rotated to isolate the tissue specimen and not just the bowed wire 22.

Embodiments of the invention may comprise other tissue specimen isolating tools with cutting members, such as is disclosed in commonly assigned U.S. Patent Applications to Burbank et al. entitled "Breast Biopsy System and Method," U.S. patent application Ser. No. 09/057,303, now U.S. Pat. No. 6,331,166, and "Tissue Specimen Encapsulation Device and Method Thereof," U.S. patent application Ser. No. 09/208,535, now U.S. Pat. No. 6,344,026, both of which are herein incorporated by reference in their entireties. Embodiments of the invention may only partially sever the tissue specimen from the surrounding tissue.

At the distal end 16 is a radio frequency wire 24 that is energized during the step of inserting the wand 12 into the surrounding tissue. Other embodiments may have other means for inserting the wand into the surrounding tissue, such as a nonenergized piercing tool or some other form of energized piercing tool. Still other embodiments of the invention may not have a piercing tool at the distal end 16, but rather enter the surrounding tissue through a pre-existing passage.

Figure 3:
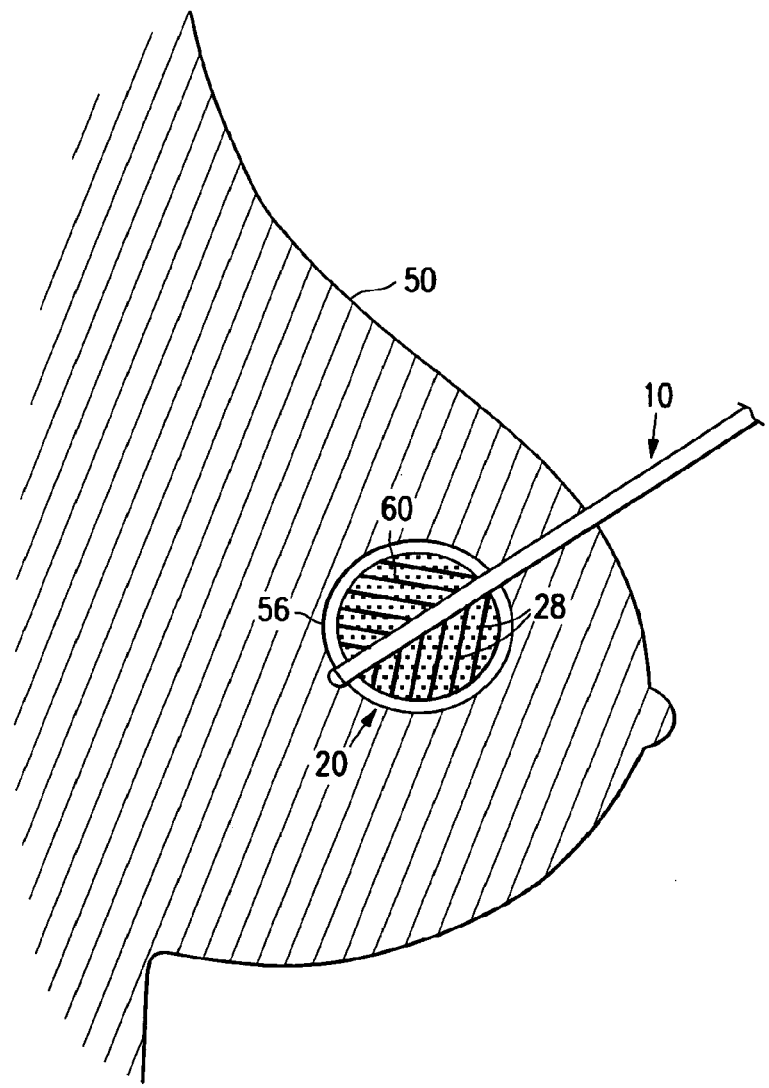
FIG. 3 shows the same sectional view as does FIG. 2 but after damaging the tissue specimen by thermal treatment.

In the shown embodiment, the tissue specimen is ablated or otherwise damaged after isolation (see FIG. 3). The damaging of the tissue sample results in necrosis. The damage may be caused by ionizing radiation that disrupts cellular functions. The tissue specimen may be damaged through mechanical means, such as cutting or otherwise morcellating the tissue specimen. Tissue specimen damage may be the result of thermal or chemical treatment.

Continuing to refer to FIG. 1, radio frequency wires 28 that extend from the operational portion 20 of the device 10 are used to damage the tissue specimen. The wires 28 are initially in a retracted position in wand 12 or disposed on the wand 12. Either before, during, or after the isolation of the tissue specimen, the wires 28 are extended as shown and enter the tissue specimen. In a preferred embodiment of the invention, the wires 28 are disposed in the wand 12 and are extended prior to isolation of the tissue specimen. The extended wires 28 anchor the device 10 in the tissue specimen, resulting in a more precise isolation of the specimen. Other embodiments of the invention may have other methods or mechanisms for anchoring, the device 10 in the tissue specimen.

The radio frequency wires 28, which comprise the tissue specimen damager of device 10, are shown extending toward the distal end 16 of the wand 12. Other embodiments of the invention may have wires 28 extending in any suitable direction. The wires 28 are shown extending almost to the radially bowed wire 22, resulting in the wires 28 being distributed throughout the tissue specimen. Other embodiments of the invention may have the wires 28 extending into a portion of the tissue specimen.

When energized, the radio frequency wires 28 damage the tissue specimen by causing the water molecules in the tissue specimen to vibrate and rapidly vaporize. The rapid vaporization results in the destruction of cells in the tissue specimen, thus damaging the specimen. The rapid vaporization is a form of thermal treatment. The radio frequency wires may be mono- or bi-polar.

After treatment, the wires 28 may be retracted into the wand 12. Other embodiments of the invention may not have the wires 28 being retracted, but rather the wires 28 remain extended and slide out of the tissue specimen during removal of the wand 12 from the surrounding tissue. The distally leaning wires 28 facilitate their sliding out of the tissue specimen during wand removal.

The severing and isolation of the tissue specimen results in a more controlled and simpler process to damage the specimen. In the case of thermal treatment, a non-isolated tissue specimen is cooled or heated by blood circulating through the specimen. The thermal treatment of an isolated tissue specimen is not competing with the cooling or heating effects of blood circulation. Without competing with the effects of blood circulation through the specimen, the thermal treatment is shorter and more restricted to the immediate tissue specimen. Further, the isolation reduces thermal damage to the surrounding tissue.

Functionally connected to the proximal end 14 of the wand 12 is a control system 30. In the shown embodiment, the control system 30 manipulates the cutting wire 22 and the radio frequency wires 28. In some embodiments of the invention, the control system 30 may control the insertion and removal of the wand 12 from the tissue specimen and the surrounding tissue. The control system 30 is functionally connected to the radio frequency generator 18 that supplies energy to the wires 22 and 28. In the embodiments of the invention in which the radially bowed wire 22 is in a fixed position on the wand 12, the control system 30 rotates the wand 12 to isolate the tissue specimen. In other embodiments of the invention, the components of the device are manipulated by hand.

Figure 2:
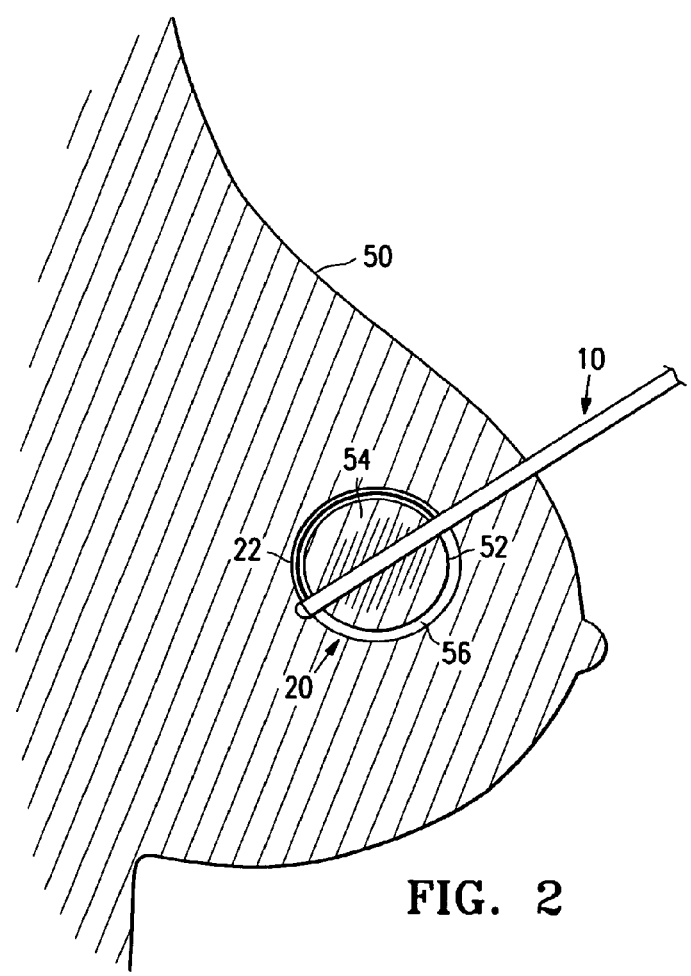
FIG. 2 shows a sectional view of the device of FIG. 1 in a breast after isolation of the tissue specimen and prior damaging the tissue specimen.

Referring now to FIG. 2, the device 10 is shown disposed in a breast 50 with the operational portion 20 being disposed in a tissue specimen 52. In this embodiment, the breast 50 may be considered the surrounding tissue. The tissue specimen 52 contains a tumor 54, which is shown cross-hatched. The cutting wire 22 is shown in the outwardly radially bowed position. The cutting wire 22 has already been rotated, thereby forming a periphery channel 56 and isolating the tissue specimen 52. Note the radio frequency wires 28 are not shown extended in FIG. 2. In a preferred embodiment of the invention, the wires 28 are extended into the tissue specimen 52 prior to isolation.

Referring now to FIG. 3, the tissue specimen 52 of FIG. 2 has been damaged, resulting in damaged tissue specimen 60 through thermal treatment by the device 10. The radio frequency wires 28 of the device 10 are shown extended into the tissue specimen 60. The wires 28 had been energized, resulting in the vaporization of the water molecules, disruption of the cells of the tissue specimen, heating the specimen, and the ultimate damaging of it. The amount and time of the treatment may be predetermined or the device may comprise a feed back system (not shown) that indicates when the treatment has been completed. In a further step, the device 10 is removed from the breast 50, either without or without retracting the radio frequency wires 28 into the device 10.

Referring now to FIG. 4, Chart 100 is a non-exclusive list of possible methods for damaging the in vivo tissue specimen besides thermal treatment through radio frequency devices. Listed as forms of thermal treatments 102 are laser, hot fluids, cold fluids, radio frequency energy and other electrosurgery techniques, microwave, focussed ultrasound, mechanical ultrasound, shock waves, resistive heating, cryosurgery using liquid or gas, cauterizing, and the application of a heated object. An example of a heated object is disclosed in U.S. Pat. No. 4,773,413 to Hussein et al. entitled "Localized Heat Applying Medical Device," which is incorporated herein by referenced in its entirety. Other embodiments of the invention may use any suitable thermal treatment system to damage the tissue specimen.

The mechanical treatment list 104 includes morcellators and other cutting devices. The ionizing radiation treatment list 106 includes treatment with x-rays, including x-ray needles, gamma rays, and Brachytherapy seeds, which are forms of ionizing radiation directors. The chemical treatment list 108 includes treatment with ethanol, sotradechol, an acid, a base, various chemical compounds, various chemical mixtures, a catalyst, a sealing agent that seals the outside of the tissue specimen, and a photoreactive chemical that is used in conjunction with a light or laser system. Other embodiments of the invention may use any suitable chemical treatment system to damage the tissue specimen.

Figure 5:
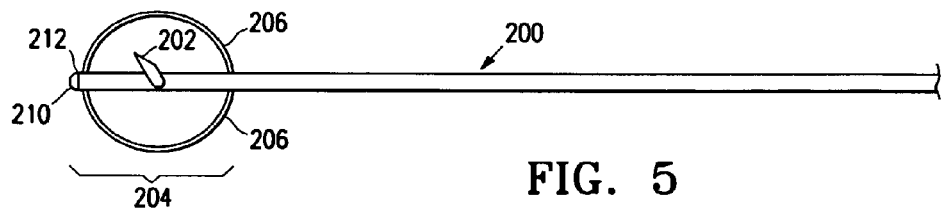
FIGS. 5-8 are side views of tissue specimen isolating and damaging devices according to various embodiments of the invention.

Referring now to FIG. 5, a tissue specimen isolating and damaging device 200 has a laser device 202 at an operational portion 204. The laser device 202 damages a tissue specimen through thermal treatment. The shown embodiment of the invention has two outwardly radially bowed cutting wires 206. Embodiments of the invention may have one or more cutting wires 206 regardless of the treatment to damage the tissue specimen. Note that a cutting tip 210 is located at a distal end 212 of the device 200.

Figure 6:
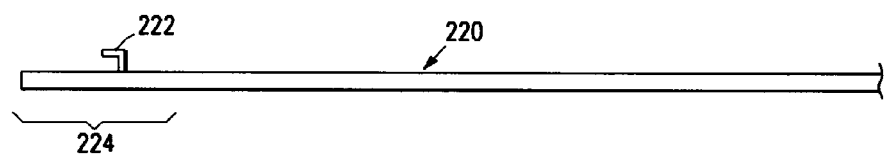

Referring now to FIG. 6, a tissue specimen isolating, and damaging device 220 has a morcellator 222 at an operational portion 224. The morcellator 222 is used to morcellate a tissue specimen. The tissue specimen may be morcellated after encapsulation of the tissue specimen. Encapsulation of the tissue specimen is disclosed in the previously referenced and incorporated U.S. patent application Ser. No. 09/208, 535, now U.S. Pat. No. 6,344,026, entitled "Tissue Specimen Encapsulation Device and Method Thereof". The tissue specimen may be encapsulated with non-biodegradable or biodegradable material. Note that there is not a piercing tool on this embodiment of the invention. Other morcellating devices may have a piercing tool. Also note that the cutting wire is in a retracted position and not visible.

In an embodiment of the invention, the tissue specimen is damaged by encapsulation. The damage is the result of the tissue specimen being physically isolated from the surrounding tissue. In an embodiment of the invention, a sheath may at least partially surround the tissue specimen (not shown).

In another embodiment of the invention (not shown), the tissue specimen may be physically isolated by encapsulation accomplished with a chemical that flows into the periphery channel about the tissue specimen and seals specimen's outside surface. Suitable techniques known in the art for ensuring a continuous distribution of the sealing chemical may be employed, such as pressurizing the periphery channel.

Figure 7:
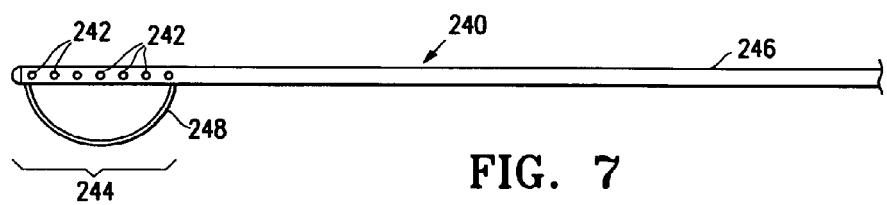

Now referring to FIG. 7, a tissue specimen isolating and damaging device 240 has outlets 242 at the operational portion 244. The outlets 242 permit the flow of a chemical into the tissue specimen, thus transforming the tissue specimen through a chemical reaction or other chemical treatment. The isolation of the tissue specimen reduces the amount of chemicals transferring to the surrounding tissue.

In other embodiments of the invention, hollow needles may extend from the operational portion 244 such that the chemical may be injected into the tissue specimen through the needles. Other embodiments of the invention may include slicing tools that make slits in the surface of the tissue specimen that is in contact with the wand 246. The slits facilitate infusion of the chemical. The slits may also be made by the cutting wire 248. The cutting wire 248 is rotated and partially extended into the tissue specimen at periodic intervals either before or after the tissue specimen has been isolated.

Figure 8:
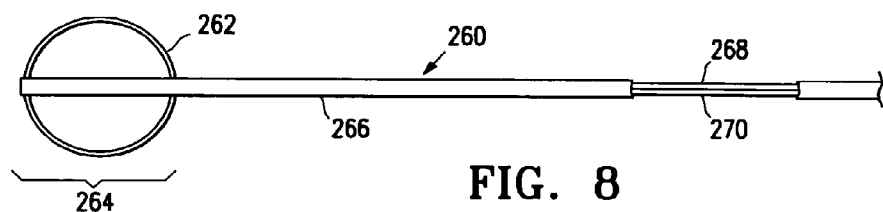

Referring now to FIG. 8, a tissue specimen isolating and damaging device 260 cryogenically treats the tissue specimen 262 disposed at the operational portion 264 of the wand 266. A cryogenic fluid is flowed to the operational portion 264 through a feed line 268 and is returned to the control system (not shown) via a return line 270, both of which is disposed in the wand 266. The tissue specimen 262 is frozen and damaged through thermal treatment with the cryogenic fluid.

Figure 9:
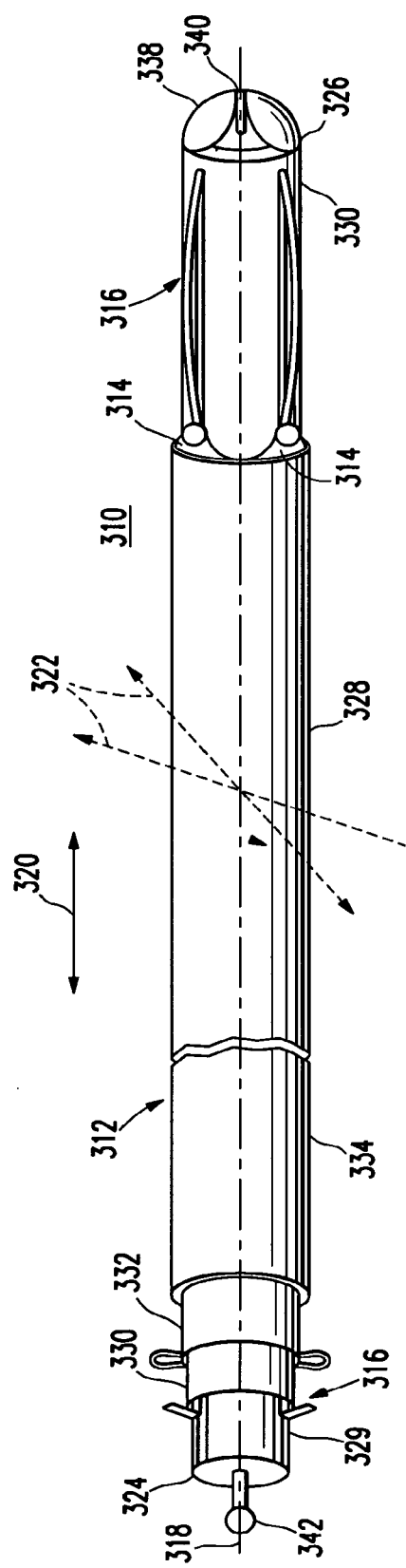
FIGS. 9 and 10 show tissue specimen encapsulation devices which may be used in conjunction with the invention.
Figure 10:
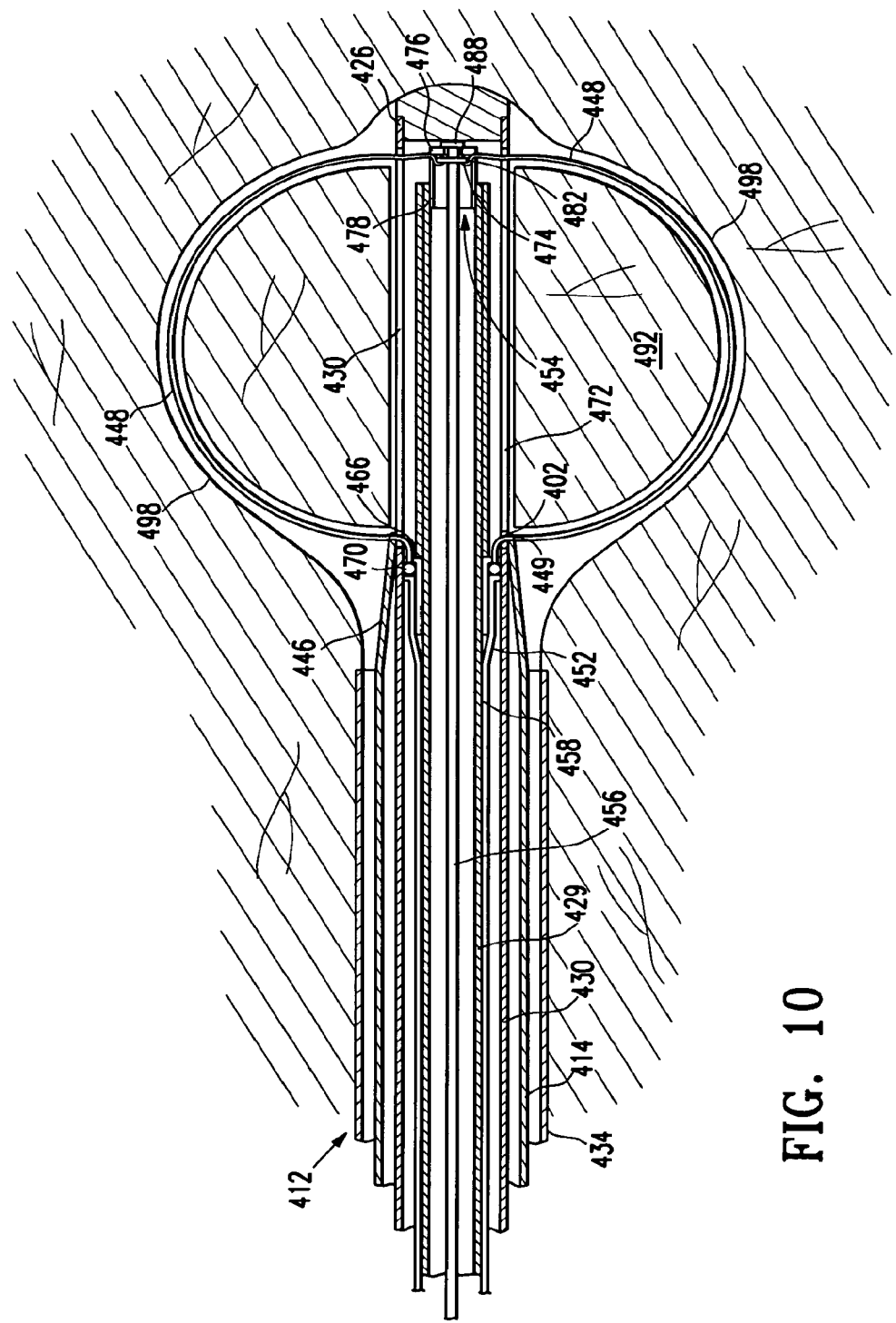

Encapsulation of the tissue specimen may be accomplished by use of a tissue specimen encapsulation device as shown in FIG. 9. The figure depicts a tissue specimen encapsulation device 310 which is comprised of a wand assembly 312, a sheath 314, and a guide assembly 316. The wand assembly 312 defines an axis 318, and axial direction 320, and a plurality of radial directions 322. The wand assembly 312 also has a proximal end 324, shown to the left in FIG. 9, and a distal end 326, shown to the right in FIG. 9. A midsection 328 extends between the ends 324 and 326. The proximal end 324 is the end that is held by a user of the device 310. The proximal end 324 may be functionally connected to an actuator system, such as a control box or the equivalent, that manipulates the device 310 per the directions of the user (not shown). The distal end 326 is inserted into a target body (not shown) and proximate to a tissue specimen to be encapsulated by the device. The wand assembly 312 may be rigid or flexible, and may be articulatable so that it may be steered. The wand assembly 312 comprises a shaft core 329, shaft 330, a sheath sleeve 332 and an outer sleeve 334. The shaft core 329, shaft 330 and sleeves 332 and 334 are co-axially aligned and nested such that the shaft core 329 is inside the shaft 330 that is inside the sheath sleeve 332 that is inside the outer sleeve 334. The shaft core 329 and the shaft 330 extend proximally and distally beyond the sleeves 332 and 334 with the shaft core extending proximally beyond the shaft. The sheath sleeve 332 extends proximally beyond the outer sleeve 334 but the outer sleeve 334 extends distally beyond the sheath sleeve 332. In the device as shown, the distal end 326 of the device 332 has a tip 338 with a radio frequency ("RF") powered member 340 extending diametrically across the tip. The RF powered member 340 may be energized such that the device moves through tissue via ablation or electrosurgical incision, thus enabling the device to be inserted into the target body containing a tissue specimen to be encapsulated. The device also may enter the biological target via other means, such as lasers or other focussed light techniques, high pressure water, cutting with a sharp implement, cryogenic techniques, etc. In addition, the device may not have a component analogous to the RF powered member 340 but the distal end 326 may be inserted into the target body through a pre-existing passage (not shown). The device also has a sheath deployment rod deployment end 342 extending from the proximal end 324 of the wand assembly 312. The sheath deployment member deployment end 342 is pulled proximally in the axial direction 320 to deploy the sheath 314 about a tissue specimen. In FIG. 10, the sheath deployment members 448 are shown deployed about the tissue specimen 492. At the axial center of the wand 412 is the sheath deployment member deployment rod 456. The sheath deployment member deployment rod 456 extends distally through the sheath deployment member cap 454 and terminates at the stop 488. The stop 488 is located distally and adjacent to the cap top 476. The sheath deployment member cap 454 is located at the distal end 426 of the wand assembly 412 with the axial extensions 478 extending proximally. The axial extensions 478 are disposed against the interior surface of the shaft core 429. The sheath deployment member deployment ends 474 are looped around the sheath deployment member ring 482, which is located proximal to the cap top 476. The sheath deployment members 448 extend from the sheath deployment member ring 482 and radially out of the distal end 426 of the shaft 430. As shown in FIG. 10, the sheath deployment member deployment rod 456 is centrally located within the shaft core 429. The push rods 452 are disposed in grooves 458 in the outer surface of the shaft core 429. The shaft 430 surrounds the shaft core 429. The tissue specimen 492 is disposed about the shaft 430 toward the shaft's distal end 426. The outer sleeve 434 is shown surrounding the shaft 430 and is located proximally from the tissue specimen 492. The sheath 414 is disposed between the shaft 430 and the outer sleeve 434 with the second portion 446 distally extending from under the outer sleeve. The sheath deployment members 448 are deployed about the tissue specimen 492 but have not been released from the wand assembly 412. The end balls 470 of the sheath deployment members 448 are disposed in the ball-holders 466. The push rods 452 have been pushed to a position proximal of ball openings 402. The ball openings 402 are located at the proximal end of each sheath deployment member slot 472 and extend through the shaft 430. The ball openings 402 generally correspond with the proximal end of the tissue specimen 492. The sheath deployment members 448 extend from the end balls 470, through the ball openings 402, through ligatures 449 extending from the sheath second portion 446, and into the periphery margin 498 about the tissue specimen 492.

Figure 11:
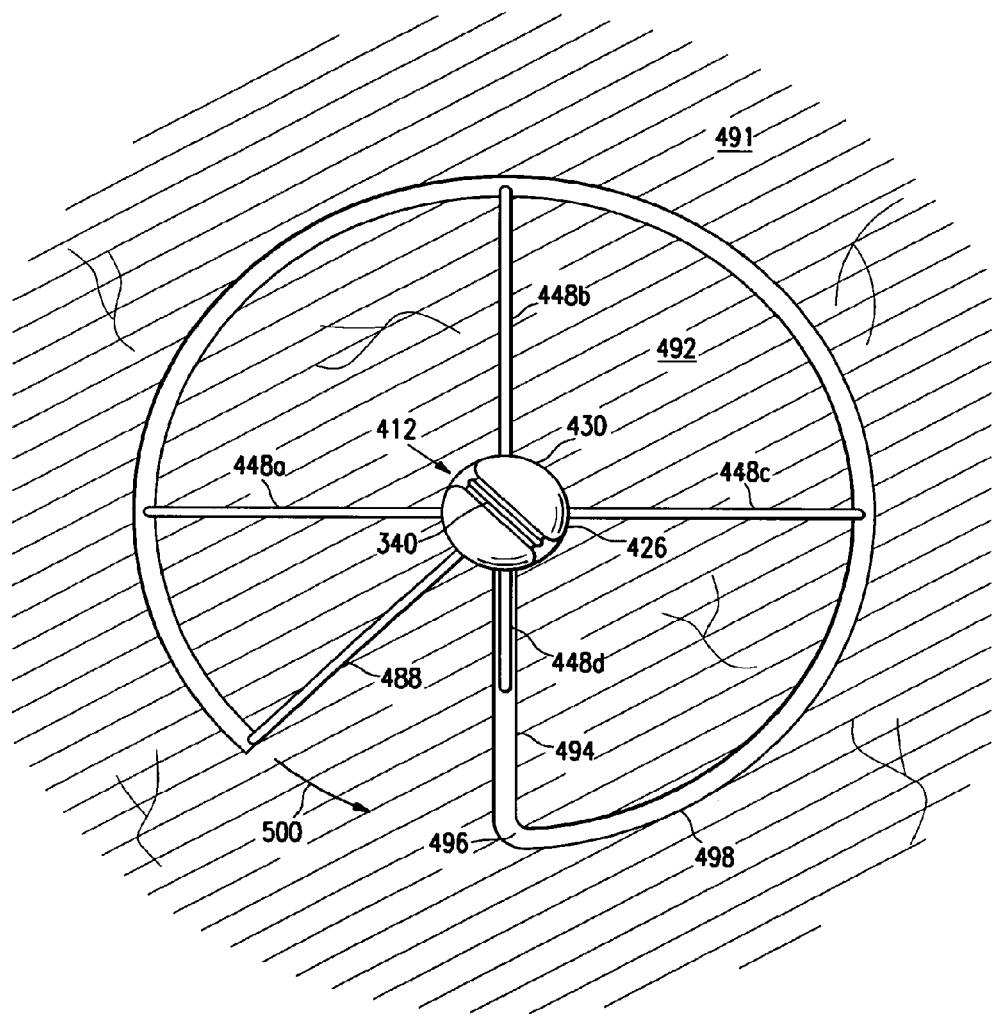
FIG. 11 is a sectional radial view of the device shown in FIGS. 9 and 10 in a target body with the sheath deployment members being partially deployed in a periphery margin surrounding the tissue specimen.

FIG. 11 shows the final sheath deployment member, sheath deployment member 448d, partially radially expanded into the channel 494 with 315 degrees of the periphery margin 498 having been formed. The remainder of the method of deploying the sheath deployment members 448 and forming the periphery margin 498 comprises fully extending the sheath deployment member 448d to point 496 and rotating the device until the cutting member 488 reaches point 496, thereby fully forming the periphery margin 498 and separating the tissue specimen 492 from the target body 491. At this point the cutting member 488 may remain bowed or may retracted at least partially back to the shaft 430 by proximally pulling its respective push rod (not shown in FIG. 6).

Figure 12:
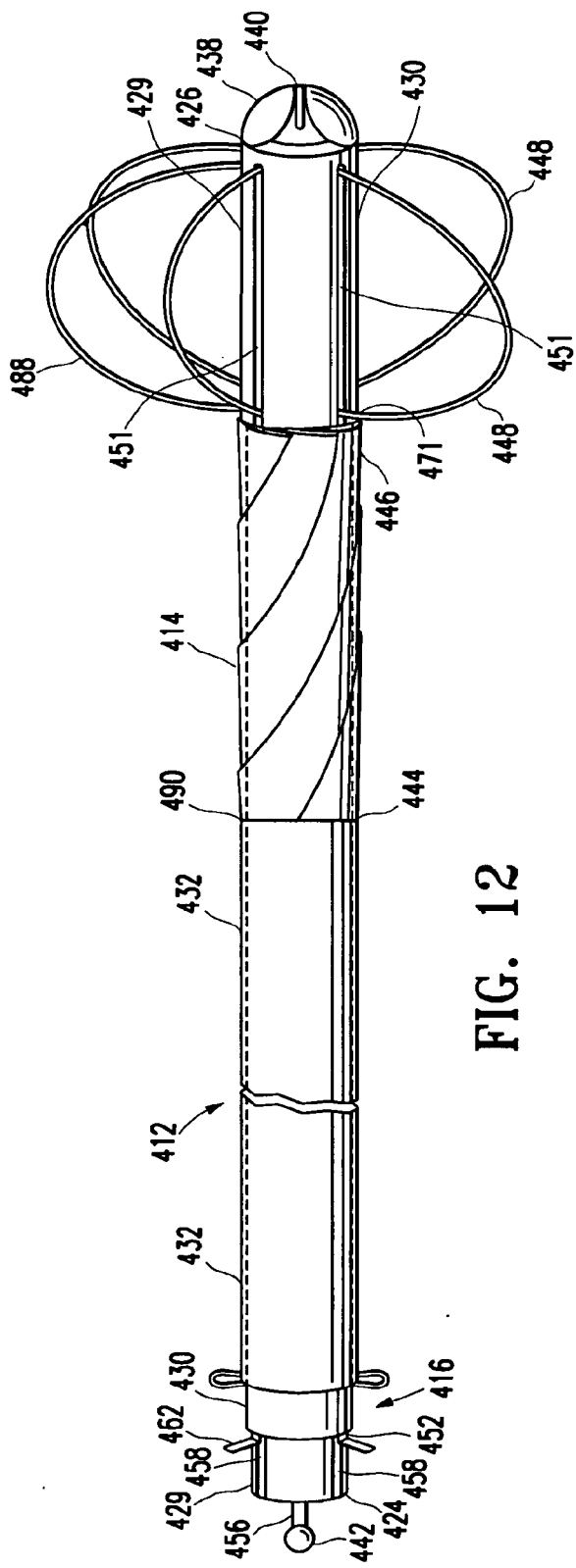
FIG. 12 is a perspective view of the device of FIGS. 9 and 10 shown without an outer sleeve and with sheath deployment members and a cutting member bowed radially outward.

Referring to FIG. 12, the sheath deployment members 448 are bowed radially outward. The bowing of the sheath deployment members 448 occurs as the respective push rods 452 are distally pushed while the distally located looped deployment end 474 (not shown, see FIG. 5) of each sheath deployment member 448 remains static. The pushing of the rods 452 moves the end balls 470 distally in the grooves 458 and forces the sheath deployment members 448 radially outward. The sheath deployment members 448 extend through ligatures 449 attached to the second portion 446 of the sheath 414. As the sheath deployment members 448 bow outwardly, the sheath deployment members slip through the holes provided until the end balls 470 comes up against the ligatures 449. The ligature 449 is a looped end of a cord 485 that is embedded in the sheath second portion 446. The ligature 449 is sized such that the end ball 470 cannot slide through it. Other embodiments of the invention may have other equivalent mechanisms and arrangements for attaching the sheath deployment member attachment end 471 to the sheath 414.

Also shown in FIG. 12 is a bowed cutting member 488 which may be a radiofrequency powered tissue cutting element. The bowed cutting member 488 is shown as being similar to the four sheath deployment members 448. The cutting member 488 is disposed and arranged in the device 410 similar to the sheath deployment members 448. Initially, the cutting member 488 is not fully bowed. Using the fifth push rod 452, the cutting member 488 is forced radially outward through slot 451. In the shown embodiment of the invention, the cutting member 488 is RF powered, as is the member 440 on the tip 438. Other embodiments of the invention may have cutting members that cut through tissue using other means. In some embodiments of the invention, the cutting member may be permanently attached to the distal end of the push rod 452. In other embodiments of the invention, the cutting member 488 may also function similar to the sheath deployment members 448 in drawing the sheath 414 over the tissue specimen as described below. In still other embodiments of the invention, there may not be element of the device 10 that functions equivalently to the cutting member 488.

Embodiments of the invention have suitable control systems incorporated into the tissue specimen isolating and damaging device. Further, the embodiments of the invention are suitably configured for different treatment methods and different tissue specimen shapes and sizes.

Although presently preferred embodiments of the present invention have been described in detail hereinabove, it should be clearly understood that many variations and/or modifications of the basic inventive concepts herein taught, which may appear to those skilled in the pertinent art, will still fall within the spirit and scope of the present invention, as defined in the appended claims.

The invention claimed is:

1. A process for operating a tissue collection apparatus having a separating device, a tissue specimen damaging device, and an encapsulating device, for collecting a tissue specimen disposed in surrounding tissue, comprising:
   isolating the tissue specimen from the surrounding tissue by using the separating device to sever and separate the tissue specimen from the surrounding tissue;
   damaging the isolated tissue specimen with the tissue specimen damaging device; and
   using the encapsulating device to encapsulate the isolated and damaged tissue specimen, the encapsulating device configured for operation independent from the separating device and the tissue specimen damaging device.

2. The process of claim 1, wherein the act of damaging includes positioning wires adjacent the isolated tissue specimen and applying radiofrequency energy to the wires.

3. The process of claim 2, wherein the wires have a free end that is extendable from a retracted position in the tissue specimen damaging device to an extended position to engage the isolated tissue specimen.

4. The process of claim 1, wherein the act of damaging includes applying ionizing radiation to the isolated tissue specimen.

5. The process of claim 1, wherein the act of damaging includes one of a morcellating and a cutting of the isolated tissue specimen.

6. The process of claim 1, wherein the act of damaging includes applying thermal energy to the isolated tissue specimen.

7. The process of claim 6, wherein the source of the thermal energy is selected from the group consisting of lasers, hot fluids, cold fluids, ultrasound, resistive heating and cryosurgery, and combinations thereof.

8. The process of claim 1, wherein the act of damaging includes introducing a tissue-damaging chemical to the isolated tissue specimen.

9. The process of claim 8, wherein the tissue-damaging chemical is selected from the group consisting of ethanol, sotradechol, acids, bases, chemical compounds, chemical mixtures, photoreactive chemicals, and sealers.

10. A tissue collection apparatus for collecting a tissue specimen, comprising:
    a tissue specimen isolation and damaging mechanism, which includes an elongate shaft; a separating device coupled to the elongate shaft and configured to separate the tissue specimen from surrounding tissue; and a tissue specimen damaging device coupled to the elongate shaft configured to operate independent from the separating device, and configured to damage the separated tissue specimen; and
    an encapsulating device coupled to the elongate shaft and configured to encapsulate the separated and damaged tissue specimen, the encapsulating device configured to operate independent from the separating device and the tissue specimen damaging device.

11. The apparatus of claim 10, wherein the tissue specimen damaging device has a plurality of radiofrequency wires, each radiofrequency wire having a free end.

12. The apparatus of claim 11, wherein the tissue specimen damaging device is configured to extend the free end of the radiofrequency wires from a retracted position within the elongate shaft to an extended position.

13. The apparatus of claim 10, wherein the tissue specimen damaging device includes an ionizing radiation source selected from the group consisting of x-ray sources, gamma ray sources, brachytherapy seeds, and combinations thereof.

14. The apparatus of claim 10, wherein the tissue specimen damaging device includes at least one of morcellators and cutters.

15. The apparatus of claim 10, wherein the tissue specimen damaging device includes at least one source of thermal energy.

16. The apparatus of claim 15, wherein the at least one source of thermal energy is selected from the group consisting of lasers, hot fluids, cold fluids, ultrasound, resistive heating and cryosurgery and combinations thereof.

17. The apparatus of claim 10, wherein the tissue specimen damaging device includes a plurality of tubular chemical introduction members that introduce a tissue-damaging chemical to the separated tissue specimen.

18. The apparatus of claim 17, wherein the tissue-damaging chemical is selected from the group consisting of ethanol, sotradechol, acids, bases, chemical compounds, chemical mixtures, and photoreactive chemicals.

* * * * *